US00PP37295P3

(12) United States Plant Patent
Fideghelli et al.

(10) Patent No.: US PP37,295 P3
(45) Date of Patent: Mar. 3, 2026

(54) GRAPEVINE PLANT NAMED 'IVC AN1'

(50) Latin Name: ***Vitis vinifera* L.**
Varietal Denomination: IVC AN1

(71) Applicant: RETE ITALIAN VARIETY CLUB, Locorotondo (IT)

(72) Inventors: Carlo Fideghelli, Locorotondo (IT); Costantino Silvio Pirolo, Locorotondo (IT); Vincenzo Roseti, Saracena (IT); Nicola Borracci, Rutigliano (IT)

(73) Assignee: RETE ITALIAN VARIETY CLUB, Locorotondo (IT)

( * ) Notice: Subject to any disclaimer, the term of this patent is extended or adjusted under 35 U.S.C. 154(b) by 0 days.

(21) Appl. No.: 18/980,088

(22) Filed: Dec. 13, 2024

(65) Prior Publication Data

US 2025/0204294 P1 Jun. 19, 2025

(30) Foreign Application Priority Data

Dec. 15, 2023 (QZ) ..... PBR 2023/2314

(51) Int. Cl.
*A01H 5/08* (2018.01)
*A01H 5/00* (2018.01)
*A01H 6/88* (2018.01)

(52) U.S. Cl.
USPC ..... Plt./207
CPC ..... *A01H 6/88* (2018.05); *A01H 5/00* (2013.01); *A01H 5/08* (2013.01)

(58) Field of Classification Search
USPC ..... Plt./207, 205
CPC ..... A01H 6/88
See application file for complete search history.

(56) References Cited

U.S. PATENT DOCUMENTS

PP3,106 P 4/1972 Garabedian
PP20,491 P2 11/2009 Striem

OTHER PUBLICATIONS

Plant Grape 1103 Paulsen retrieved on Mar. 10, 2025 at https://www.plantgrape.fr/en/varieties/rootstock-varieties/23/export, 3 pp. (Year: 2023).*
Upov Pluto 20250307 retrieved on Mar. 10, 2025 at https://pluto.upov.int/result, one page (Year: 2025).*

* cited by examiner

*Primary Examiner* — June Hwu
(74) *Attorney, Agent, or Firm* — Foley & Lardner LLP

(57) ABSTRACT

This invention relates to a new and distinct variety of grapevine plant named 'IVC AN1'. The new variety is primarily adapted to the growing conditions of the temperate or dry areas, e.g. southern Italy, with low rainfall and low disease pressure (namely downy mildew), with winter minimum temperatures down to 10° C., and is characterized by attractive berries with vivid greenish yellow color which are uniform in size and shape and are firm with tender crunchy skin.

4 Drawing Sheets

Figure 1:
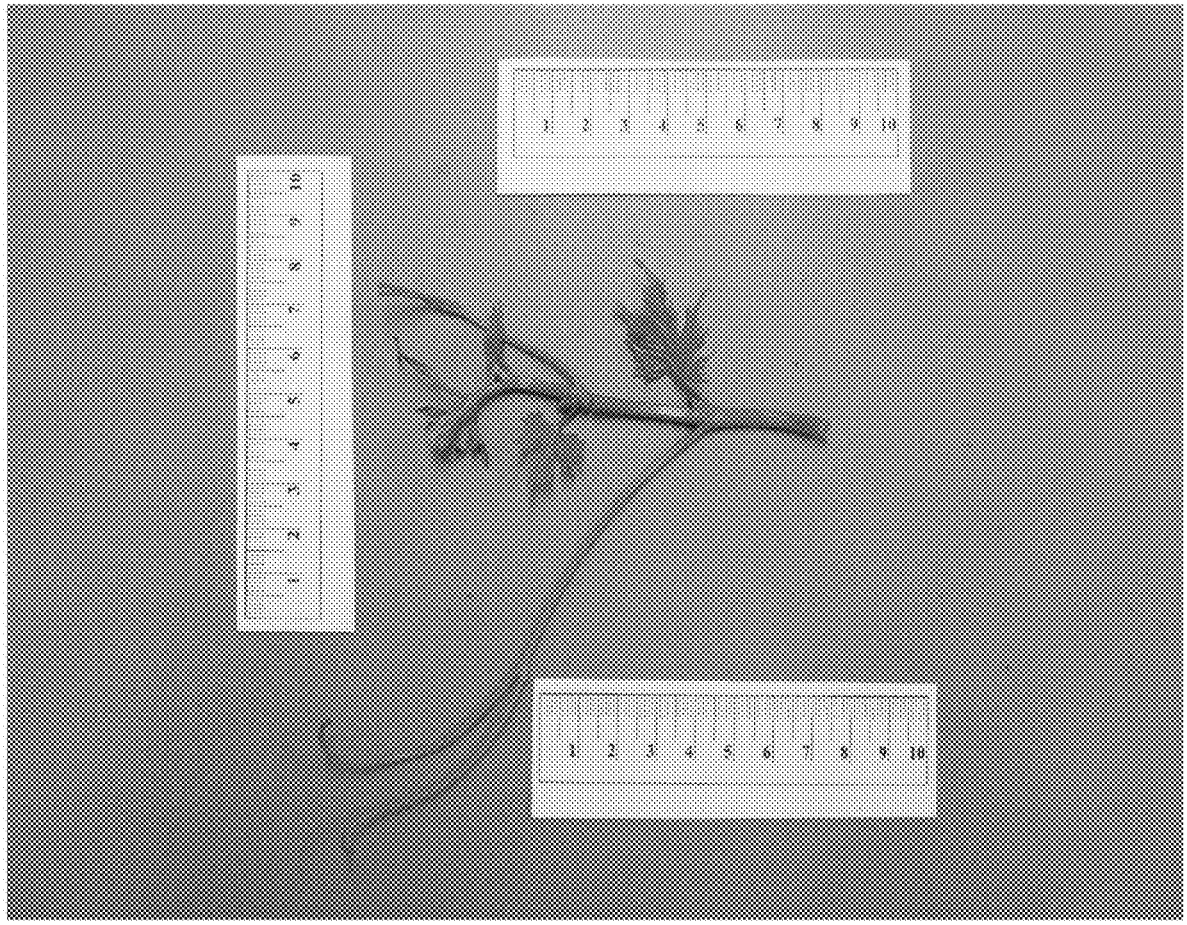

Botanical name of the genus and species of the plant claimed: *Vitis vinifera* L.

Variety denomination: 'IVC AN1'.

CROSS-REFERENCE TO RELATED APPLICATION

This application claims priority from Community Plant Variety Rights Application No. 2023/2314, filed Dec. 15, 2023.

BACKGROUND OF THE INVENTION

The present invention relates to a new and distinct grapevine variety, botanically known as *Vitis vinifera* L., and hereinafter referred to by its variety denomination 'IVC AN1'.

The new grapevine 'IVC AN1' is a product of a controlled breeding program conducted by the inventors, Professors Carlo Fideghelli, Silvio Costantino Pirolo, Nicola Borracci, and Vincenzo Roseti, at Azienda Martucci Valenzano (BA). The objective of the breeding program was to develop a new early ripening, very fertile grapevine variety particularly characterized by attractive berries with yellowish green color which are uniform in size and shape and are firm with tender crunchy skin.

'IVC AN1' is primarily adapted to the climate and growing conditions of the temperate regions with average yearly temperature about 19° C., minimum winter temperature about −10° C., annual rainfall around 500-750 mm of rain (e.g. south-Eastern Italy, Puglia). This region provides the necessary year-round temperatures required for it to produce and maintain a strong vigorous plant with consistent fruit production.

The new grapevine 'IVC AN1' originated from a cross made by the inventors in 2021 at Puglia, Italy. The female or seed parent is the grapevine *Vitis vinifera* L. indicated as 'IVC A23' (unpatented), in the inventors' collection located in Valenzano (Bari) Apulia, Italy, and the male or pollen parent is the grapevine *Vitis vinifera* L. indicated as 'IVC A42' (unpatented), in the inventors' collection.

The new grapevine 'IVC AN1' was observed and selected by the inventors within the progeny of the stated cross in a controlled environment in 2022, 2023, and 2024, at Valenzano (BA), Italy.

Asexual propagation of the new grapevine variety by bud grafting was first performed in 2022 in Valenzano (BA), Italy, and has demonstrated that the combination of characteristics as herein disclosed for the new variety is firmly fixed and retained through successive generations of asexual propagation. The new cultivar propagates true-to-type.

SUMMARY OF THE INVENTION

'IVC AN1' can be grown in various climates and growing conditions. The variety produces and maintains a strong vigorous plant and consistent fruit production from August to September in Valenzano (BA), Italy.

The following traits have been repeatedly observed and are determined to be characteristics of 'IVC AN1', which in combination distinguish this grapevine as a new, unique, and distinct variety.

1. Very fertile;
2. Medium ripening;
3. Firm berry with tender crunchy skin;
4. Attractive vivid greenish yellow berry color;
5. Uniform berries;
6. Vigor: medium;
7. Growth habit: erect;
8. Leaf: medium size, medium to dark green color (upper surface), light green color (lower surface), pentagonal shape, medium texture of pubescence on the lower surface;
9. Medium size cluster, two medium size wings, loose or medium dense, berry skin with golden-green colour with amber nuances in the sunny side of berry, crunchy flesh, aromatic taste, no flesh coloration, use: table, maturity: mid-August (Middle Puglia, south-Eastern Italy);
10. Green shoots: oblate cross section, brownish colour, lenticels: absent, short- middle internodes, diameter: 8 mm; and
11. Harvesting time: medium (late August in middle Puglia).

Plants of the new grapevine 'IVC AN1' differ from plants of the parents *Vitis vinifera* L. 'IVC A23' (unpatented) and *Vitis vinifera* L. 'IVC A42' (unpatented), in the following characteristics described in Table 1.

TABLE 1

COMPARISON WITH PARENT VARIETIES

| Characteristic | New Variety 'IVC ANI' | Female Parent 'IVC A23' (unpatented) | Male Parent 'IVC A42' (unpatented) |
|---|---|---|---|
| Berry shape | Ovoid | globose | Ovoid |
| Berry color of skin | Yellow/ green | yellow | yellow |
| Berry thickness of skin | subtle | subtle | subtle |
| Seeds | absent | absent | absent |

Of the many commercial varieties known to the present inventors, the most similar to the new grapevine 'IVC AN1' are *Vitis vinifera* L. 'SUGRATHIRTYFIVE', U.S. Plant Pat. No. 20,491 P2, and 'SUPERIOR SEEDLESS', U.S. Plant Pat. No. 3,106, which differ from the new grapevine 'IVC AN1' in the characteristics described in Table 2.

TABLE 2

COMPARISON WITH SIMILAR VARIETIES

| Characteristic | New Variety 'IVC ANI' | Comparison Variety 'SUGRATHIRTYFIVE' (PP20,491 P2) |
|---|---|---|
| Berry shape | ovoid | globose |
| Berry color of skin | yellow/ green | yellow |
| Berry thickness of skin | subtle | subtle |
| Seeds | absent | absent |

| Characteristic | Comparison Variety 'SUPERIOR SEEDLESS' (PP03106) |
|---|---|
| Berry shape | ovoid |
| Berry color of skin | yellow |
| Berry thickness of skin | not very thin |
| Seeds | absent |

BRIEF DESCRIPTION OF THE PHOTOGRAPHS

The accompanying photographs illustrate the overall appearance of the new grapevine 'IVC AN1' showing the colors as true as is reasonably possible with colored reproductions of this type. Colors in the photographs may differ slightly from the color values cited in the detailed morphological description, which accurately describe the color of 'IVC AN1'.

Figure 2:
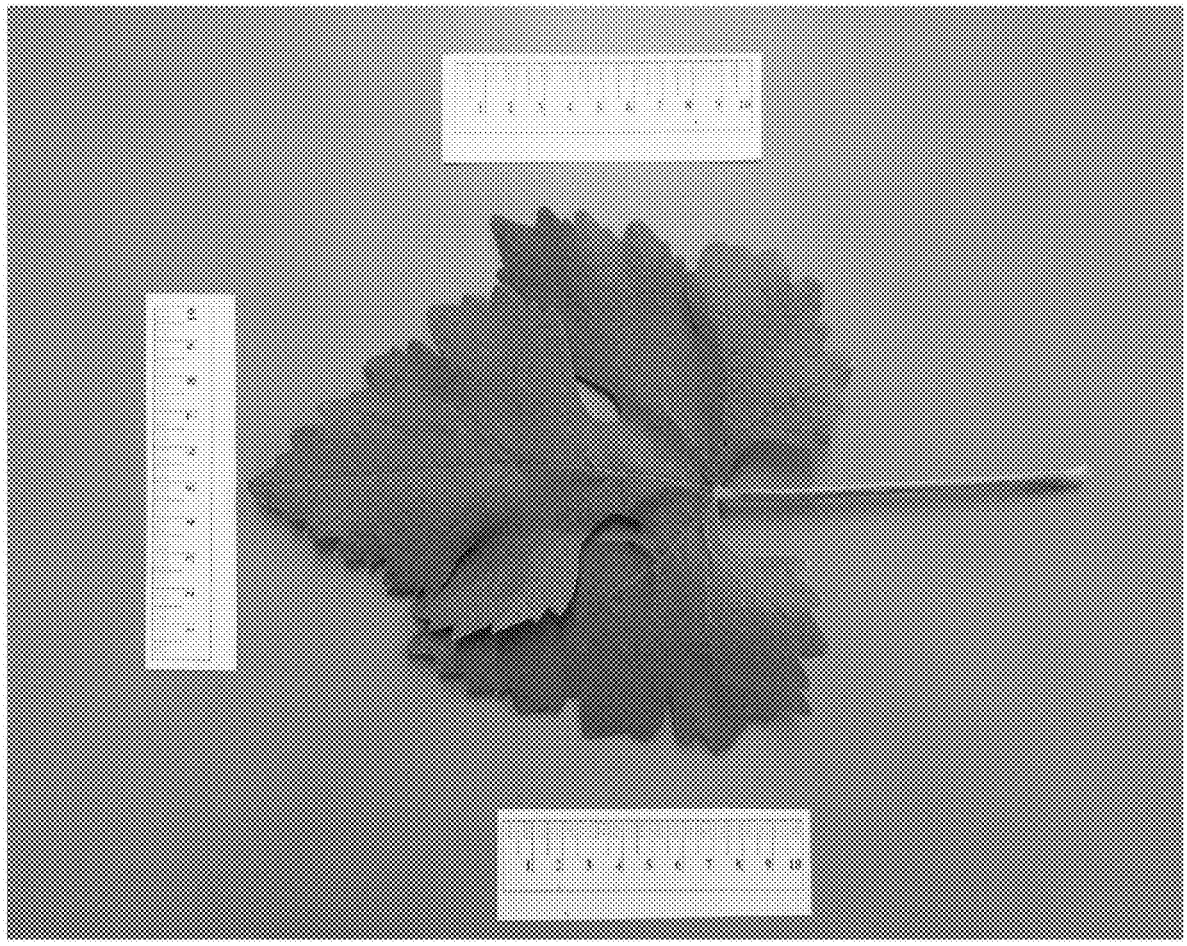
Figure 3:
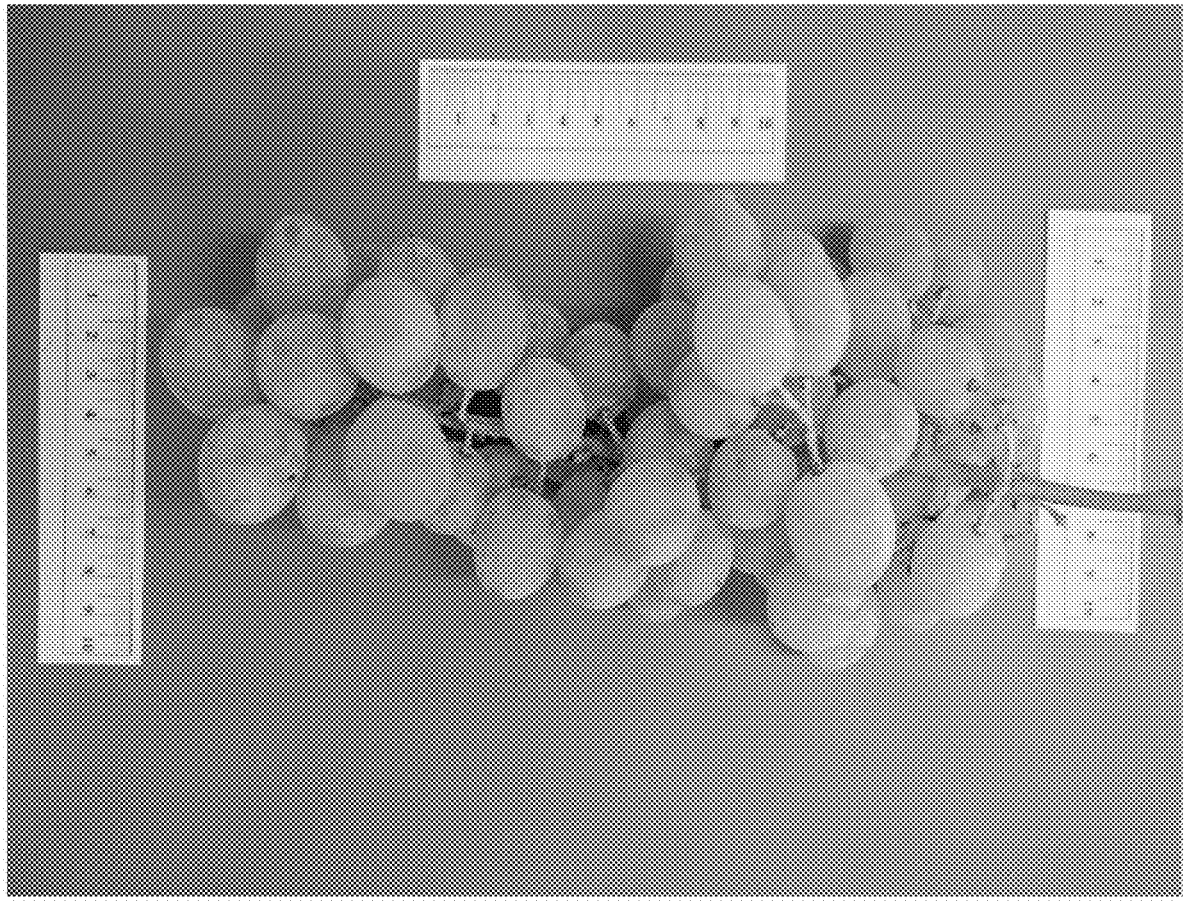
Figure 4:
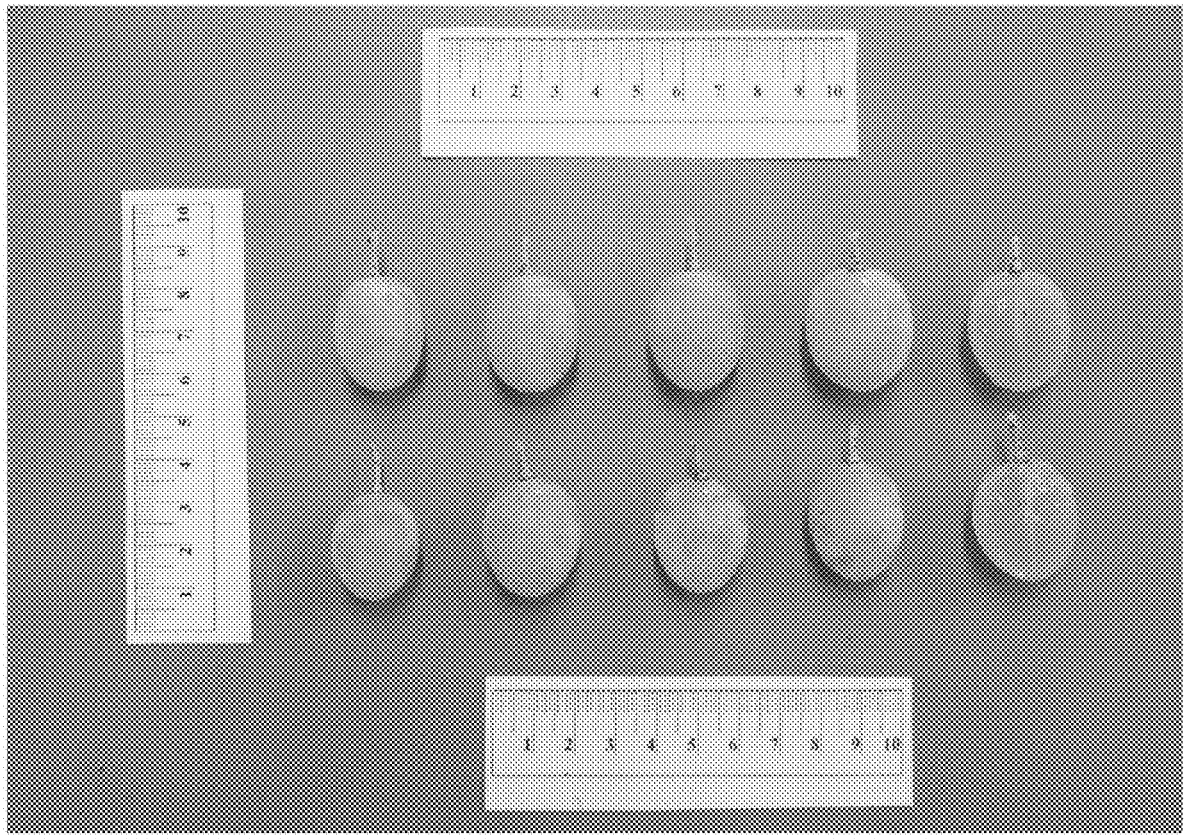

FIG. 1 shows the typical young shoot of 'IVC AN1'.
FIG. 2 shows the typical mature leaf of 'IVC AN1'.
FIG. 3 shows the typical fruit cluster of 'IVC AN1'.
FIG. 4 shows the typical mature fruit of 'IVC AN1'.

DETAILED MORPHOLOGICAL DESCRIPTION

The new *Vitis vinifera* L. 'IVC AN1' has not been observed under all possible environmental conditions. The phenotypical descriptions and color designations stated for the new variety may vary, depending on variations in environmental factors, including weather (temperature, humidity and light intensity), day length, soil type, location and cultural conditions, without any change in the genotype of the grapevine.

The following description of 'IVC AN1' unless otherwise noted, is based on observations and measurements taken during 2022, 2023 and 2024, on plants grown in the vineyard located in Valenzano (BA)—Apulia, Italy under conditions which closely approximate those generally used in commercial practice. The described plants were grafted on 140 Ru and 1103 P. 'IVC AN1' planted at a distance of 2.5 m in typical red loam soil at an elevation of about 150 meter above sea level with drip-irrigation up to 2500 mq per hectare in the peak season in the summer and 25 kg of micro-elements L. fertilizers in each 9.600,00 liter of water. Average annual rainfall is about 550 mm, with an average of 350 mm rainfall in winter (December through February). Mean diurnal minimum temperature in January is 3.3° C., and mean diurnal maximum temperature in July is 29° C.

Unless otherwise stated, the detailed morphological description includes observations, measurements and values based on 3-year-old 'IVC AN1' plants grown in the vineyard at Valenzano (BA), Italy from 2022 to 2024. Quantified measurements are expressed as an average of measurements taken from a number of plants of '30'. The measurements of any individual plant, or any group of plants, of the new variety may vary from the stated average. Color references are made to The Royal Horticultural Society Colour Chart (R.H.S.) 2015 edition. Color values were taken under daylight conditions in full sunlight in Valenzano (BA), Italy. All of the plants of 'IVC AN1', insofar as they have been observed, have been consistent in all the characteristics described below.

Classification:

*Botanical.*—*Vitis vinifera* L.

Parentage:

*Female or seed parent.*—*Vitis vinifera* L. 'IVC A23' (unpatented).

*Male or pollen parent.*—*Vitis vinifera* L. 'IVC A42' (unpatented).

Propagation: Grafting.

Growing conditions:

*Light intensities.*—70.000 lux.

*Temperature.*—28° C.

*Location.*—Valenzano (BA), Italy.

TABLE 3

| MEAN | | | | | | |
|---|---|---|---|---|---|---|
| | January | February | March | April | May | June |
| Mean maximum air temperature (° C.) | | | | | | 29 |
| Mean minimum air temperature (C.) | 3.3 | | | | | |
| Mean rainfall (mm) | 10<br>0 | 150 | 100 | | | 0 |
| | July | August | September | October | November | December |
| Mean maximum air temperature (° C.) | | | | | | |
| Mean minimum air temperature (C.) | | | | | | |
| Mean rainfall (mm) | | | | 50 | 100 | 50 |

*Fertilization.*—Organic and mineral.

*Pruning.*—To 50 gems.

*Training.*—4 branches.

TABLE 4 OF CHARACTERISTICS

Plant:

*Time of vegetative bud burst.*—Beginning of April.

Young shoot:

*Openness of tip.*—Fully open.

*Density of prostrate hairs on tip.*—Very low.

*Anthocyanin coloration of prostrate hairs on tip.*—Very low.

*Green color.*—Medium green — RHS 128A.

*Green color of upper side of undeveloped leaf blade.*—Light green — RHS 134C.

*Green color of lower side of undeveloped leaf blade.*—Light green — RHS 134C.

*Anthocyanin coloration.*—Very low.

Young leaf:

*Density of hairs between main veins on lower side of blade.*—Very sparse.

*Glossiness of upper side.*—Medium green — RHS 128A.

*Glossiness of lower side.*—Medium green — RHS 128A.

Shoot:

*Length of internode.*—12 cm.

*Thickness of internode.*—1.8 cm.

*Color of dorsal side of internode.*—Medium green — RHS 128A.

*Anthocyanin coloration of dorsal side of internode.*—Absent.

*Distribution of anthocyanin coloration of dorsal side of internode.*—Absent.

*Color of ventral side of internode.*—Light green — RHS 134C.

*Anthocyanin coloration of ventral side of internode.*—Absent.

*Distribution of anthocyanin coloration of ventral side of internode.*—Absent.

*Erect hairs on internodes.*—Absent.

*Height of node.*—Medium.

*Swelling at node.*—Absent.

*Diameter of node.*—2.2 cm.

*Color of dorsal side of node.*—Medium green — RHS 128A.

*Anthocyanin coloration of dorsal side of node.*—Absent.

*Distribution of anthocyanin coloration of dorsal side of node.*—Absent.

*Color of ventral side of node.*—Medium green — RHS 128A.

*Anthocyanin coloration of ventral side of node.*—Absent.

*Distribution of anthocyanin coloration of ventral side of node.*—Absent.

*Pubescence of node.*—Very low.

*Length of tendril.*—15-20 cm.

*Diameter of tendril at base.*—0.2-0.3 cm.

*Diameter of tendril at tip.*—Medium.

*Pubescence of tendril.*—Very low.

*Number of bifurcations per tendril.*—1.

*Color of tendril.*—Light green — RHS 134C.

*Anthocyanin coloration of tendril.*—Very low or absent.

*Number of consecutive tendrils.*—2 or less.

Inflorescence:
*Length.*—25-35 cm.
*Maximum diameter.*—0.5 cm.
*No. of side branches.*—2.
*Attitude of side branches.*—Medium.
*Length of longest side branch.*—10 cm.
*Thickness of main axis.*—Medium.
*Green color of main axis.*—Light green — RHS 134C.
*Anthocyanin coloration of main axis.*—Absent.
*Pubescence of main axis.*—Absent.
Flower:
*Sexual organs.*—Complete.
*Full bloom.*—End of May.
Pedicel:
*Length.*—0.4 cm.
*Thickness.*—Medium or large.
*Green color.*—Light green — RHS 134C.
*Pubescence.*—Absent.
Stamen:
*Number.*—5.
*Length of filament.*—0.2 cm.
*Thickness of filament.*—Medium or large.
*Pubescence of filament.*—Absent.
*Surface.*—Smooth.
*Color.*—Light green — RHS 134C.
Anther:
*Shape.*—Elongated.
*Length.*—Medium.
*Color.*—Light yellow — RHS 14D.
Pollen:
*Color.*—Light yellow — RHS 14D.
Ovary:
*Shape.*—Elongated.
*Color.*—Light green — RHS 134C.
*Length.*—0.15 cm.
*Diameter.*—0.12 cm.
*Surface.*—Smooth.
Style:
*Length.*—Medium.
Stigma:
*Size.*—Medium.
*Color.*—Light green — RHS 134C.
Mature leaf:
*Blade length.*—12-22 cm.
*Blade width.*—16-18 cm.
*Shape of blade.*—Pentagonal.
*Green color of upper side.*—RHS 128A.
*Green color of lower side.*—RHS 128A.
*Glossiness of upper side.*—Very low.
*Glossiness of lower side.*—Very low.
*Profile in cross section.*—Twisted.
*Blistering of upper side.*—Very low.
*Number of lobes.*—5.
*Central lobe length.*—10-12 cm.
*Central lobe width.*—8 cm.
*Upper, side lobe length.*—8-10 cm.
*Upper, side lobe width.*—6-8 cm.
*Pubescence of veins on upper side.*—Very low.
*Pubescence of veins on lower side.*—Low.
*Green color of veins on upper side.*—Moderate.
*Green color of veins on lower side.*—Tenuous.
*Anthocyanin coloration of veins on upper side.*—Absent.
*Anthocyanin coloration of veins on lower side.*—Absent.
*Depth of upper lateral sinus.*—Deep.
*Arrangement of lobes of upper leaf sinus.*—Superimposed.
*Arrangement of lobes of petiole sinus.*—Open.
*Petiole sinus limited by veins.*—Not delimited.
*Length of distal tooth.*—1.6 cm.
*Width of distal tooth.*—1.4 cm.
*Ratio length/width of distal tooth.*—Medium.
*Shape of tooth.*—Mixture of both sides straight and both sides convex.
*Anthocyanin coloration of main veins on upper side of blade.*—Absent.
*Density of hairs between veins on upper side of blade.*—Very low.
*Density of hairs between veins on lower side of blade.*—Low.
*Length of petiole compared to main vein.*—Similar.
*Length of petiole.*—Long.
*Petiole thickness.*—Medium.
Petiole:
*Green color of upper side.*—Light green — RHS 134C.
*Anthocyanin coloration of upper side.*—High.
*Green color of lower side.*—Light green — RHS 134C.
*Anthocyanin coloration of lower side.*—High.
*Pubescence.*—Absent or very low.
Fruit:
*Time of beginning of berry ripening.*—August 10-20$^{th}$.
Bunch:
*Length (peduncle included).*—250 mm.
*Maximum diameter.*—150 mm.
*Weight.*—g. 650.
*General shape.*—Funnel shaped.
*Peduncle length.*—4-6 cm.
*Peduncle thickness.*—Medium.
*Peduncle color.*—Green RHS 129A.
*Peduncle lignification.*—Basal lignification.
*Density.*—Medium.
Pedicel:
*Length.*—8 mm.
*Thickness.*—Medium.
*Color.*—Light green — RHS 134C.
Berry:
*Detachment.*—Not easy.
*Length.*—26 mm.
*Diameter.*—24 mm.
*Weight.*—High 5.5 g.
*Shape in profile.*—Spherical.
*Shape in cross section.*—Globose.
*Depression at distal end.*—Very low.
*Color of skin (without bloom).*—Light yellow — RHS 2A.
*Amount of bloom.*—Medium.
*Surface.*—Smooth.
*Thickness of skin.*—Medium.
*Adherence of skin to flesh.*—High.
*Flesh color.*—No flesh coloration.
*Flesh anthocyanin coloration.*—Absent.
*Firmness of flesh.*—Medium.
*Juiciness of flesh.*—Medium.
*Particular flavor.*—Neutral.
*Formation of seeds.*—Absent.
*Number of berries per primary bunch.*—250.
*Acidity (titratable acidity).*—5 g/l.
*Sweetness (brix percentage).*—20° Brix.

Woody shoot:

*Length of node*.—Medium.

*Main color* (*without bloom*).—Light green — RHS 134C.

*Relief of surface*.—Low.

*Shape in cross section*.—Circular.

*Diameter*.—2.5-3.5 cm.

*Lenticels*.—Very low.

Trunk:

*Vigor*.—Medium.

*Size*.—10 cm (observed height of 1 mt).

*Color*.—Dark Brown — RHS 166A.

*Characteristics*.—Longitudinal flaking.

Usage: Table grape.

Disease\pest resistance: No atypical resistance has been noted.

Shipping quality: Mostly packed in 5-10 cartons.

Storage life and productivity: The grapes can be easily stored in the refrigerator for over a month. Productivity is 25 kg for plants in average conditions and on young plants.

What is claimed is:

1. A new and distinct variety of grapevine plant named 'IVC AN1', substantially as illustrated and described herein.

* * * * *